(12) United States Patent
Drauz et al.

(10) Patent No.: US 6,294,681 B1
(45) Date of Patent: Sep. 25, 2001

(54) PROCESS FOR THE PRODUCTION OF N-ACYLAMINO ACIDS

(75) Inventors: Karlheinz Drauz, Freigericht; Olaf Burkhardt, Alzenau-Hoerstein; Matthias Beller, Rostock; Markus Eckert, Cologne; Wahed Moradi; Helfried Neumann, both of Rostock, all of (DE)

(73) Assignee: Degussa-Huels AG, Hanau (DE)

( * ) Notice: Subject to any disclaimer, the term of this patent is extended or adjusted under 35 U.S.C. 154(b) by 0 days.

(21) Appl. No.: 09/604,274

(22) Filed: Jun. 26, 2000

(30) Foreign Application Priority Data

Jun. 25, 1999 (GB) .......................................... 199.29 079.2
Mar. 14, 2000 (GB) .......................................... 100.12 251.5

(51) Int. Cl.$^7$ ................................................. C07C 231/00
(52) U.S. Cl. .............................................. 554/69; 554/68
(58) Field of Search ........................................ 554/69, 68

*Primary Examiner*—Deborah D. Carr
(74) *Attorney, Agent, or Firm*—Oblon, Spivak, McClelland, Maier & Neustadt, P.C.

(57) ABSTRACT

The present invention provides a process for producing N-acyl-protected amino acids with the general formula I

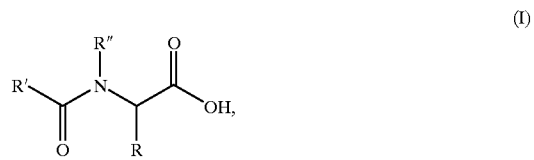

by amidocarbonylation whereby carbon monoxide, an amide/nitrile and an aldehyde, are reacted in the presence of a metal catalysts such as rhodium, iridium or ruthenium catalysts.

22 Claims, No Drawings

PROCESS FOR THE PRODUCTION OF N-ACYLAMINO ACIDS

DESCRIPTION OF THE INVENTION

The invention relates to a process for the production of N-acylamino acids with the general formula I

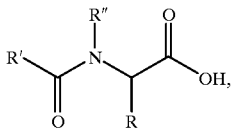

where
- R denotes hydrogen, a carboxyl group, a unsaturated or saturated, straight-chain, branched or cyclic ($C_1$–$C_{12}$) alkyl group, a mono- or polyunsaturated, straight-chain, branched or cyclic($C_2$–$C_{12}$) alkenyl radical, and a ($C_1$–$C_8$) acyloxy group, a ($C_4$–$C_8$) aryl radical, and ($C_1$–$C_{12}$) alkyl ($C_4$–$C_{18}$) aryl radical,
- R' and R" independently and separately denote hydrogen, a saturated, straight-chain, branched or cyclic ($C_1$–$C_{26}$) alkyl, a mono- or polyunsaturated, straight-chain, branched or cyclic ($C_2$–$C_{24}$) alkenyl radical, a ($C_1$–$C_{12}$) alkyl ($C_4$–$C_{18}$) aryl radical or an optionally polyunsaturated ($C_2$–$C_{10}$) alkenyl ($C_4$–$C_{18}$) aryl radical.

BACKGROUND OF THE INVENTION

N-acylamino acids are important starting products in peptide synthesis and intermediates for the production of biologically active agents. Moreover, N-acylamino acids are useful in detergents, drilling agent additives and food additives.

The manufacture of N-acylamino acids by acylation of corresponding amino acids with accumulation of salt by-products is known in the art. Regarding non-natural amino acids, the corresponding amino acid must frequently be manufactured in a number of stages. A single-stage process that avoids these disadvantages is the amidocarbonylation of aldehydes and amides, which is illustrated in the following diagram.

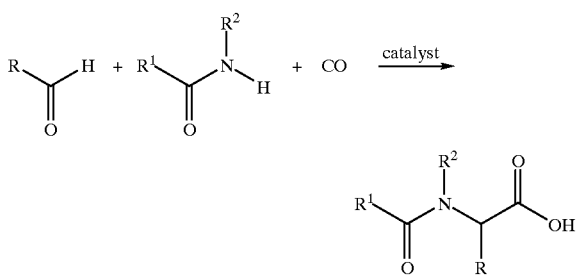

Amidocarbonylation was first described by Wakamatsu et al., (Chemical Communications 1971, page 1540 and in DE-A2-21 15 985). The carbonylation is performed in the presence of hydrogen gas with a 3:1 molar ratio of CO:$H_2$. The cobalt carbonyl complex $Co_2(CO)_8$ is used as catalyst in a concentration of 30 mmol Co metal per litre of reaction mixture.

A further cobalt-catalysed process based on amidocarbonylation is described in GB 2 252 770. In this reaction the synthesis of N-acylamino acids is performed by reacting carboxylic acid amide with an aldehyde and CO in the presence of a metal catalyst and an acid co-catalyst.

EP-B-0 338 330 describes a process for the production of N-acylglycine derivatives with a catalyst system consisting of a palladium compound and an ionic halide. DE 195 45 641 and DE 196 29 717 describe a process for the preparation of N-acylglycine derivatives from a carboxylic acid amide and an aldehyde with palladium catalysis. In these reactions, ionic halides and additional acid may be used as co-catalysts.

DE 199 20 107.2 describes amidocarbonylation starting from nitrites in the presence of palladium or cobalt catalysts.

It is known from the literature that carboxylic acid amides react with aldehydes and carbon monoxide to N-acylamino acids. Until now only palladium and cobalt complexes have been used as catalysts for this reaction. Against this background it is surprising for the person skilled in the art that rhodium, iridium and ruthenium complexes also catalyze the reaction of amides with aldehydes and carbon monoxide. The reactions proceed with very high selectivities and good catalyst productivities. Unreacted educt can be readily recovered by recovery processes familiar to the person skilled in the art (distillation, crystallization) and can be reused, such that good yields can also be obtained in continuous processes.

SUMMARY OF THE INVENTION

An object of the present application is to provide further substances for amidocarbonylation that can catalyze said reaction.

Another object of the present invention is a process for producing N-acylamino acids of the formula I by reacting an amide of the formula II, an aldehyde of formula III in the presence of an acid, carbon monoxide, and a metal catalyst.

Another object of the present invention is the process for producing N-acylamino acids of the formula I in a dipolar aprotic solvents or solvent mixtures.

Another object of the present invention is producing enantiomer enriched N-acylamino acids by chiral modification and using the enantiomer enriched N-acylamino acids in the process for producing N-acylamino acids of the formula I.

DETAILED DESCRIPTION OF THE INVENTION

The invention provides a process for the production of N-acylamino acids of the formula I

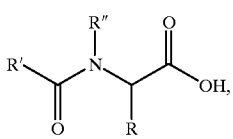

wherein
- R is selected from hydrogen, a carboxyl group, a saturated or unsaturated, straight-chain, branched or cyclic ($C_1$–$C_{12}$) alkyl group, a mono- or polyunsaturated, straight-chain, branched or cyclic($C_2$–$C_{12}$) alkenyl radical, a ($C_1$–$C_8$) acyloxy group, a ($C_4$–$C_{18}$) aryl radical, and a ($C_1$–$C_{12}$) alkyl ($C_4$–$C_{18}$) aryl radical,
- R' and R" independently and separately are selected from hydrogen, a saturated, straight-chain, branched or cyclic ($C_1$–$C_{26}$) alkyl, a mono- or polyunsaturated, straight-chain, branched or cyclic ($C_2$–$C_{24}$) alkenyl radical, a ($C_1$–$C_{12}$) alkyl ($C_4$–$C_{18}$) aryl radical or an optionally polyunsaturated ($C_2$–$C_{10}$) alkenyl ($C_4$–$C_{18}$) aryl radical, reacting an amide with the formula II

R'—CO—NH—R"                    (II), in which R' and R" have the meaning given above, and an aldehyde with the formula III

R—CHO                             (III), in which R has the meaning given above,
in the presence of carbon monoxide and a metal catalyst selected from rhodium, iridium or ruthenium catalysts. This process advantageously yields the desired compounds of formula I.

According to the invention, any amides as educts can be used as starting materials. Examples of suitable amides are acetamide, benzamide, propionamide, N-methylacetamide, fatty acid amides, acrylamide, cinnamic acid amide, phenylacetic acid amide, acetanilide and urea. In the process according to the invention the amide component can also be optionally manufactured in situ from corresponding nitrites, for example by acid-catalyzed hydrolysis. Examples of suitable nitrites are acetonitrile, benzonitrile, substituted benzonitriles, benzyl cyanide, acrylonitrile, malonic dinitrile, adiponitrile, butyl cyanide, allyl cyanide, mandelic acid nitrile and fatty acid nitriles.

For the process according to the invention, any aldehydes may be used, e.g., formaldehyde, acetaldehyde, propionaldehyde, butyraldehyde, valeraldehyde, 2-ethylhexanal, isobutyraldehyde, furfural, crotonaldehyde, acrolein, benzaldehyde, substituted benzaldehydes, phenylacetaldehyde, 2,4-dihydroxyphenylacetaldehyde, glyoxylic acid and α-acetoxypropionaldehyde. Dialdehyde compounds may also be used. Substances that can form an aldehyde under the stated reaction conditions, e.g., aldehyde oligomers are also suitable. Examples of such aldehyde oligomers paraformaldehyde, acetals, allyl alcohols and epoxies.

The aldehyde is conveniently used in a quantity of 0.5 to 5 equivalents, preferably 0.8 to 2 equivalents, relative to the amide. Included in this range is 0.75, 1.0, 1.5, 2.0, 2.5, 3.0, 3.5, 4.0, 4.5 equivalents, and all values and subranges there between.

The aldehydes may be used in the reaction in the form of their trimers or oligomers.

Active metal catalysts for the reaction may be any catalyst known in the art and which are based on rhodium, ruthenium or iridium.

Metal carbonyls or metal halides or metal carboxylates are preferably used as the rhodium, ruthenium or iridium catalysts or pre-catalysts. Typical catalysts or precatalysts are rhodium (III) acetate, rhodium (III) chloride, acetylacetonato-bis(ethylene) rhodium(I), bis(1,5-cyclooctadiene) rhodium (I) trifluoromethane sulfonate, chloro-bis(ethylene) rhodium (I) dimer, chloro(1,5-cyclooctadiene) rhodium (I) dimer, chlorodicarbonyl rhodium (I) dimer, chloro-tris(triphenylphosphane) rhodium (I), hexarhodium hexadecacarbonyl, dicarbonyl acetylacetonatrhodium (I), rhodium (III) acetylacetonate, rhodium (II) acetate dimer, tetrarhodium dodecacarbonyl, acetatodicarbonyl ruthenium, bis(cyclopentadienyl) ruthenium, dichloro-bis[(p-cymene)chlororuthenium (II)], dichloro(1,5-cyclooctadienyl) ruthenium (II), dichlorodicarbonyl-bis (triphenylphosphane) ruthenium (II), dichloro-tris (triphenylphosphane) ruthenium (II), ruthenium (III) acetylacetonate, ruthenium (III) chloride, ruthenium carbonyl, chlorocarbonyl-bis(triphenylphosphane) iridium (I), chloro-1,5-cyclooctadienyl iridium (I) dimer, chlorotricarbonyl iridium (I), iridium (III) acetylacetonate, iridium (III) chloride and iridium carbonyl.

The addition of ligands has proven beneficial when using the above-noted metal catalysts. Phosphanes such as triarylphosphanes, trialkylphosphanes and arylalkylphosphanes are particularly used as ligands. The use of phosphanes with one or more chiral centers also allows enantiomer-pure N-acylamino acids or N-acylamino acids enriched with an enantiomer to be produced in the reaction.

In particular all N- or P-containing ligands familiar to the person skilled in the art are suitable. Examples of nitrogen ligands are phenthrolines, bis-imidazolines, and benzylamines. These and other such ligands are described, for example, in A. Togni, L. M. Venanzi "Stickstoffdonoren in der Organometailchemie und in der Homogenkatalyse", Angew. Chemie, 1994, 106, 517, incorporated herein by reference. Preferred chiral phosphines are deguphos, ferriophos, and BPPM. Preferred achiral phosphines are triphenylphosphane, tri-o-toluylphosphane, tricyclohexylphosphane, tri-tert-butylphosphane, bis-diphenylphosphinoethane, bis-diphenylphosphinopropane, bis-diphenylphosphinobutane and bis-diphenylphosphinopentane These and other chiral or achiral phosphines are described, for example, in H. Brunner, W. Zettelmeier "Handbook of Enantioselective Catalysis, VCH Weinheim, 1993, incorporated herein by reference.

The above-mentioned catalysts may also be used as carrier-bound catalysts. In principle all materials familiar to the person skilled in the art are suitable as carrier materials, in particular, carrier materials such as carbon, aluminium oxide, titanium oxide, silicon oxide, barium sulfate, and the like are suitable for use. Carbon is particularly preferred as a carrier.

According to the present invention a quantity of from 0.0001 to 5 mol % catalyst (calculated on catalyst metal), preferably from 0.001 to 4 mol % and particularly preferably from 0.01 to 2 mol % relative to the amide and all values and subranges there between is sufficient.

Additionally advantageous is to add an ionic halide as co-catalyst.

Phosphonium bromides and phosphonium iodides, e.g., tetrabutyl phosphonium bromide or tetrabutyl phosphonium iodide, also ammonium, lithium, sodium, potassium chloride, bromide and iodide can be used as halides. Preferred halides are chlorides and bromides. The ionic halide is preferably used in a quantity of 1 to 100 mol %, particularly 2–40 mol % and most particularly 5–30 mol %, relative to the amide, including 3, 7, 9, 14, 18, 22, 29, 35, 45, 50, 55, 60, 70, 80, 90 mol % and all values and subranges therebetween.

In an advantageous embodiment of the process, the addition of acid as a cocatalyst frequently produces better results. Examples of acids that can be used include sulfuric acid, HCl, HBr, trifluoromethane sulfonic acid, acetic acid, phosphoric acid, nitric acid, and the like. The acid is generally used in this context in catalytic quantities, preferably in quantities of 0.1–10 mol % and particularly preferably 0.5 to 5 mol % relative to the amide. These ranges include 0.2, 0.3, 0.4, 0.6, 0.7, 0.8, 0.9, 1, 1.5, 2.0, 2.5, 3.0, 3.5, 4.0, 4.5, 5.5, 6.0, 6.5, 7.5, 8.0, 8.5, 9.0, 9.5 and all values and subranges therebetween.

If the amidocarbonylation is started from nitrites, saponification of the amides may also be initiated by using the acids disclosed above. Preferred acids to be used have a pKa value of not more than 4. Sulfuric acid or a hydrogen halide, such as hydrogen chloride or hydrogen bromide, can preferably be used in this reaction. Mixtures of such acids may also be used. As a particularly preferred variant, a mixture of a strong acid such as sulfuric acid or hydrogen bromide can be used in the presence of formic acid. The formic acid can be used in 1–100 equivalents relative to the nitrile.

As solvents for the reaction under consideration, all organic compounds familiar to the person skilled in the art can in principle be used. Dipolar aprotic compounds are preferably used. Examples of these include dioxan, tetrahydrofuran, N-methylpyrrolidone, ethyleneglycol dimethylether, ethyl acetate, acetic acid, acetonitrile, benzonitrile, tert-butylmethylether, butylmethylether, dibutylether, sulfolan, N,N-dimethylacetamide or mixtures thereof. The solvents can be used in pure form or product-containing or saturated with product. N-methylpyrrolidone, dimethylformamide and acetonitrile are preferred as solvents.

The reaction may be performed at pressures of from 1 to 250 bar, preferably from 10 to 150 bar, including 5, 15, 20, 25, 40, 50, 60, 70, 80, 90, 100, 110, 130, 160, 175, 190, 200, 215, 225 bar and all values and subranges there between. The reaction may be performed at temperatures of 0 to 200° C., preferably from 50 to 150° C., including 5, 10, 15, 30, 40, 60, 75, 90, 110, 130, 145, 160, 175, 190° C. and all values and subranges there between.

When the present process starts from nitrile, the process can be performed as in a single reaction vessel or, preferably, in two stages. In the two-stage process the nitrile is first dropped into a mixture of water and an acid, e.g., concentrated. sulfuric acid. After addition of solvent, aldehyde, catalyst and ionic halide the mixture is reacted with carbon monoxide. High yields of N-acylamino acid are obtained in the overall process.

If desired, the reaction may also be performed in a single stage. For example, the aldehyde, the catalyst compound and the halide are dissolved in the nitrile, and this mixture is dropped into the acid/water mixture and reacted to the end product in the presence of carbon monoxide.

Moreover, simple access to enantiomer-enriched N-acylamino acids can be obtained by chiral modification of the metal catalyst. Examples of such chiral modified metal catalysts are disclosed in Catalytic Asymmetric Syntheis, Iwao Ojima (ed.), Wiley-VCH, 1992, pp. 445–463 incorporated herein by reference.

A ($C_4$–$C_{18}$) aryl radical is understood to denote, for example, an optionally substituted phenyl, naphthyl, anthryl, phenanthryl, biphenyl radical or a five-, six- or seven-membered heteroaromatic optionally having nitrogen, oxygen or sulfur atoms in the ring, whereby these radicals may be substituted with fluorine, chlorine, bromine, iodine, OH, $NO_2$, CN, $CO_2H$, CHO, $SO_3R'''$, $SO_2R'''$, $SOR'''$, $NHCOR'''$, $COR'''$, NHCHO, COAr, $CO_2A$, $CF_3$, $CONH_2$, $CHCHCO_2R'''$, $SiR'''$, $POAr_2$, $POR'''$. $R'''$ denotes a ($C_1$–$C_{12}$) alkyl radical, which may be saturated, straight-chain, branched or cyclic, a ($C_2$–$C_{12}$) alkenyl radical, which may be mono- or polyunsaturated, straight-chain, branched or cyclic.

A ($C_1$–$C_{12}$) alkyl radical is understood to denote an alkyl radical with one to twelve carbon atoms, all of which contain bonding isomers such as would be conceivable for such a radical. This may also be a carbocyclic compound. The same applies to the ($C_2$–$C_{24}$) alkenyl radical. A ($C_1$–$C_8$) acyloxy radical is understood to denote a linear or branched alkyl group with one to eight carbon atoms together with all conceivable bonding isomers for this radical, which is bonded to the molecule by means of a carbonyloxy function.

The alkyl and alkenyl groups occurring in the radical R, R' and R" may be substituted with fluorine, chlorine, bromine, iodine, OH, $NO_2$, CN, $CO_2H$, CHO, $SO_3R'''$, $SO_2R'''$, $SOR'''$, $NHCOR'''$, $COR'''$, NHCHO, COAr, $CO_2Ar$, $CF_3$, $CONH_2$, $CHCHCO_2R'''$, $SiR'''$, $POAr_2$, $POR'''$.

Ar is a ($C_4$–$C_{18}$) aryl radical.

$R'''$ denotes a ($C_1$–$C_{12}$) alkyl radical, which may be saturated, straight-chain, branched or cyclic, a ($C_2$–$C_{12}$) alkenyl radical, which may be mono- or polyunsaturated, straight-chain, branched or cyclic.

Having generally described this invention, a further understanding can be obtained by reference to certain specific examples which are provided herein for purposes of illustration only, and are not intended to be limiting unless otherwise specified.

EXAMPLES

Example 1

A 10% solution of 25 mmol cyclohexylcarbaldehyde and 25 mmol acetamide in N-methylpyrrolidone are reacted with 0.25 mol % chloro-1,5-cyclooctadienyl iridium dimer, 0.5 mol % triphenylphosphane, 0.10 g sulfuric acid and 35 mol % LiBr in a 300 ml autoclave with 60 bar carbon monoxide at 100° C. After a reaction time of 12 h the solvent is removed in vacuo and the residue is analyzed by HPLC.

Yield: 30%

Selectivity: 90% N-acetylcyclohexylglycine

Turnover number: 108

Example 2

A 10% solution of 25 mmol cyclohexylcarbaldehyde and 25 mmol acetamide in N-methylpyrrolidone are reacted with 0.25 mol % chloro-1,5-cyclooctadienyl iridium, 0.5 mol % triphenylphosphane, 0.10 g sulfuric acid and 35 mol % LiBr in a 300 ml autoclave with 60 bar carbon monoxide at 100° C. After a reaction time of 24 h the solvent is removed in vacuo and the residue analyzed by HPLC.

Yield: 46%

Selectivity: 89% N-acetylcyclohexylglycine

Turnover number: 176

Example 3

A 10% solution of 25 mmol cyclohexylcarbaldehyde and 25 mmol acetamide in N-methylpyrrolidone are reacted with 0.25 mol % chloro-1,5-cyclooctadienyl iridium, 0.5 mol % triphenylphosphane, 0.10 g sulfuric acid and 35 mol % LiBr in a 300 ml autoclave with 25 bar carbon monoxide at 100° C. After a reaction time of 12 h the solvent is removed in vacuo and the yield analyzed by means of HPLC.

Yield: 14%

Selectivity: 93% N-acetylcyclohexylglycine

Turnover number: 52

Example 4

A 10% solution of 25 mmol cyclohexylcarbaldehyde and 25 mmol acetamide in N-methylpyrrolidone are reacted with 0.25 mol % carbonylchloro-bis(triphenylphosphane) iridium, 0.5 mol % triphenylphosphane, 0.10 g sulfuric acid and 35 mol % LiBr in a 300 ml autoclave with 60 bar carbon monoxide at 100° C. After a reaction time of 12 h the solvent is removed in vacuo and the residue analyzed by means of HPLC.

Yield: 28%
Selectivity: 93% N-acetylcyclohexylglycine
Turnover number: 104

Example 5

A 10% solution of 25 mmol cyclohexylcarbaldehyde and 25 mmol acetamide in N-methylpyrrolidone are reacted with 0.25 mol % carbonylchloro-bis(triphenylphosphane) iridium, 0.5 mol % triphenylphosphane, 0.10 g trifluoroacetic acid and 1 eq LiBr in a 300 ml autoclave with 60 bar carbon monoxide at 100° C. After a reaction time of 12 h the solvent is removed in vacuo and the residue analyzed by means of HPLC.
Yield: 28%
Selectivity: 93% N-acetylcyclohexylglycine
Turnover number: 104

Example 6

A 10% solution of 25 mmol benzaldehyde and 25 mmol acetamide in N-methylpyrrolidone are reacted with 0.25 mol % chloro-1,5-cyclooctadienyl iridium dimer, 0.5 mol % triphenylphosphane, 0.10 g sulfuric acid and 35 mol % LiBr in a 300 ml autoclave with 60 bar carbon monoxide at 100° C. After a reaction time of 12 h the solvent is removed in vacuo and the residue analyzed by means of HPLC.
Yield: 12%
Selectivity: 96% N-acetylphenylglycine
Turnover number: 44

Example 7

A 10% solution of 25 mmol isobutyraldehyde and 25 mmol acetamide in N-methylpyrrolidone are reacted with 0.25 mol % chloro-1,5-cyclooctadienyl iridium dimer, 0.5 mol % triphenylphosphane, 0.10 g sulfuric acid and 35 mol % LiBr in a 300 ml autoclave with 60 bar carbon monoxide at 100° C. After a reaction time of 12 h the solvent is removed in vacuo and the residue analyzed by means of HPLC.
Yield: 29%
Selectivity: 97% N-acetylvaline
Turnover number: 112

Example 8

A 10% solution of 25 mmol cyclohexylcarbaldehyde and 25 mmol acetamide in N-methylpyrrolidone are reacted with 0.50 mol % ruthenium (III) chloride, 1.0 mol % triphenylphosphane, 0.10 g sulfuric acid and 35 mol % LiBr 30 in a 300 ml autoclave with 60 bar carbon monoxide at 120° C. After a reaction time of 12 h the solvent is removed in vacuo and the residue analyzed by means of HPLC.
Yield: 11%
Selectivity: 91% N-acetylcyclohexylglycine
Turnover number: 20

Example 9

A 10% solution of 25 mmol cyclohexylcarbaldehyde and 25 mmol acetamide in N-methylpyrrolidone are reacted with 0.25 mol % dichloro-tris(triphenylphosphane) ruthenium, 0.5 mol % triphenylphosphane, 0.10 g sulfuric acid and 35 mol % LiBr in a 300 ml autoclave with 60 bar carbon monoxide at 100° C. After a reaction time of 12 h the solvent is removed in vacuo and the residue analyzed by means of HPLC.
Yield: 12%
Selectivity: 92% N-acetylcyclohexylglycine
Turnover number: 22

Example 10

A 10% solution of 25 mmol cyclohexylcarbaldehyde and 25 mmol acetamide in N-methylpyrrolidone are reacted with 0.25 mol % rhodium trichloride, 0.5 mol % triphenylphosphane, 0.10 g sulfuric acid and 35 mol % LiBr in a 300 ml autoclave with 60 bar carbon monoxide at 120° C. After a reaction time of 12 h the solvent is removed in vacuo and the residue analyzed by means of HPLC.
Yield: 18%
Selectivity: 83% N-acetylcyclohexylglycine
Turnover number: 60

Example 11

A 10% solution of 25 mmol cyclohexylcarbaldehyde and 25 mmol acetamide in N-methylpyrrolidone are reacted with 0.25 mol % rhodium (III) acetylacetonate, 0.10 g sulfuric acid and 35 mol % LiBr in a 300 ml autoclave with 60 bar carbon monoxide at 120° C. After a reaction time of 12 h the solvent is removed in vacuo and the residue analyzed by means of HPLC.
Yield: 21%
Selectivity: 86% N-acetylcyclohexylglycine
Turnover number: 72

Example 12

A 10% solution of 25 mmol cyclohexylcarbaldehyde and 25 mmol acetamide in N-methylpyrrolidone are reacted with 0.25 mol % rhodium (II) acetate dimer, 0.10 g sulfuric acid and 35 mol % LiBr in a 300 ml autoclave with 60 bar carbon monoxide at 120° C. After a reaction time of 12 h the solvent is removed in vacuo and the residue analyzed by means of HPLC.
Yield: 20%
Selectivity: 96% N-acetylcyclohexylglycine
Turnover number: 72

Example 13

A 10% solution of 25 mmol benzaldehyde and 25 mmol acetamide in N-methylpyrrolidone are reacted with 0.25 mol % rhodium (III) acetylacetonate, 0.10 g sulfuric acid and 35 mol % LiBr in a 300 ml autoclave with 60 bar carbon monoxide at 120° C. After a reaction time of 12 h the solvent is removed in vacuo and the residue analyzed by means of HPLC.
Yield: 21%
Selectivity: 86% N-acetylphenylglycine
Turnover number: 72

The priority documents DE 199 29079.2 filed Jun. 25, 1999 and DE 100 12251.5 filed Mar. 14, 2000 are hereby incorporated in their entirety by reference.

Obviously, numerous modifications and variations on the present invention are possible in light of the above teachings. It is therefore to be understood that within the scope of the appended claims, the invention may be practiced otherwise than as specifically described herein.

What is claimed is:
1. A process for producing N-acylamino acids with the general formula I

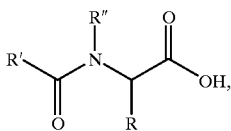

(I)

wherein
R is selected from the group consisting of hydrogen, a carboxyl group, a saturated or unsaturated, straight-chain, branched or cyclic ($C_1$–$C_{12}$) alkyl group, a mono- or polyunsaturated, straight-chain, branched or cyclic ($C_2$–$C_{12}$) alkenyl radical, a ($C_1$–$C_8$) acyloxy group, a ($C_4$–$C_{18}$) aryl radical, and a ($C_1$–$C_{12}$) alkyl ($C_4$–$C_{18}$) aryl radical, R', and R" independently are selected from the group consisting of hydrogen, a saturated, straight-chain, branched or cyclic ($C_1$–$C_{26}$) alkyl, a mono- or polyunsaturated, straight-chain, branched or cyclic ($C_2$–$C_{24}$) alkenyl radical, a ($C_1$–$C_{12}$) alkyl ($C_4$–$C_{18}$) aryl radical and a optionally polyunsaturated ($C_2$–$C_{10}$) alkenyl ($C_4$–$C_{18}$) aryl radical, comprising reacting an amide with the general formula II

wherein R' and R" have the meaning given above, and an aldehyde with the general formula III

wherein R has the meaning given above, in the presence of an acid, carbon monoxide and a metal catalyst selected from the group consisting of rhodium catalyst, iridium catalyst and ruthenium catalyst.

2. The process according to claim 1, wherein the aldehyde is in amount from 0.5 to 5 equivalents relative to the amide.

3. The process according to claim 1, wherein the aldehyde is in amount from 0.8 to 2 equivalents relative to the amide.

4. The process according to claim 1, wherein the aldehyde is a trimer or oligomer.

5. The process according to claim 1, wherein the metal catalyst is selected from the group consisting of a rhodium$^{0,1+,2+,3+}$ compound, ruthenium$^{0,2+,3+}$ compound and iridium$^{0,1+,3+}$ compound.

6. The process according to claim 1, further comprising adding P- or N-containing ligands to the metal catalyst.

7. The process according to claim 5, wherein the catalyst is in an amount from 0.0001 to 5 mol % relative to the amide.

8. The process according to claim 7, the catalyst is in an amount from 0.01 to 2 mol % relative to the amide.

9. The process according to claim 1, wherein the process further comprises adding a halide salt.

10. The process according to claim 9, wherein the halide salt is in an amount from 0.1 to 100 mol % relative to the amide.

11. The process according to claim 9, wherein the halide salt is in an amount from 2 to 40 mol % relative to the amide.

12. The process according to claim 1, wherein the acid has a pKa value of not more than 4.

13. The process according to claim 12, wherein the acid is sulfuric acid or hydrogen halide.

14. The process according claim 12, further comprising adding formic acid to the reaction.

15. The process according to claim 1, wherein the reaction is performed in dipolar aprotic solvents or solvent mixtures.

16. The process according to claim 15, wherein the solvents are selected from the group consisting of N-methylpyrrolidine, dimethylformamide and acetonitrile.

17. The process according to claim 1, wherein the reaction is performed at a carbon monoxide gas pressure of from 1 to 250 bar.

18. The process according to claim 1, wherein the reaction is performed at a carbon monoxide gas pressure of from 10 to 150 bar.

19. The process according to claim 1, wherein the reaction is performed at a temperature of from 0 to 200° C.

20. The process according to claim 1, wherein the reaction is performed at a temperature of from 50 to 150° C.

21. The process according to claim 1, wherein is performed in a single stage starting from a nitrile.

22. The process according claim 1, wherein the metal catalyst is chirally modified to produce enantiomer enriched N-acylamino acids.

* * * * *